United States Patent
Hayashi et al.

(10) Patent No.: US 10,327,729 B2
(45) Date of Patent: Jun. 25, 2019

(54) RADIOGRAPHIC IMAGING SYSTEM

(71) Applicant: KONICA MINOLTA, INC., Chiyoda-ku (JP)

(72) Inventors: Naoki Hayashi, Higashimurayama (JP); Tomohiko Hagi, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 15/693,642

(22) Filed: Sep. 1, 2017

(65) Prior Publication Data
US 2018/0008225 A1 Jan. 11, 2018

Related U.S. Application Data

(62) Division of application No. 14/600,876, filed on Jan. 20, 2015, now abandoned.

(30) Foreign Application Priority Data

Jan. 23, 2014 (JP) .................. 2014-010186

(51) Int. Cl.
A61B 6/00 (2006.01)

(52) U.S. Cl.
CPC ............ *A61B 6/566* (2013.01); *A61B 6/4233* (2013.01); *A61B 6/4283* (2013.01);
(Continued)

(58) Field of Classification Search
CPC ... A61B 6/4233; A61B 6/4283; A61B 6/4494; A61B 4/467; A61B 6/545; A61B 6/548; A61B 6/566
See application file for complete search history.

(56) References Cited

U.S. PATENT DOCUMENTS

| | | | |
|---|---|---|---|
| 8,644,454 B2 * | 2/2014 | Yonekawa | A61B 6/00 378/115 |
| 9,072,484 B2 * | 7/2015 | Yonekawa | A61B 6/00 |
| 2010/0104065 A1 * | 4/2010 | Eguchi | A61B 6/00 378/62 |

(Continued)

FOREIGN PATENT DOCUMENTS

| CN | 103202700 | 7/2013 |
|---|---|---|
| CN | 104545958 | 4/2015 |

(Continued)

OTHER PUBLICATIONS

Office Action dated Jul. 4, 2017 which issued in the corresponding Japanese Patent Application No. 2014101186.

(Continued)

*Primary Examiner* — Wyatt A Stoffa
(74) *Attorney, Agent, or Firm* — Cozen O'Connor

(57) ABSTRACT

Radiographic imaging system comprising an x-ray radiation source. Multiple radiographic imaging apparatuses, each including multiple radiation detecting elements, are arranged two-dimensionally, and configured to read charges generated in the radiation detecting elements as image data and transmit an image signal in response to a command. A console communicating with, controlling with a command the operation of, and receiving image signals from, the multiple radiographic imaging apparatuses and acquires multiple radiographing order information items indicating which of the multiple radiographic imaging apparatuses is to be used for conducting radiographing. Upon receiving the image signal from a first of the radiographic imaging apparatuses, the console determines from the multiple radiographing order information items a subsequent radiographing order item to be conducted by the first radiographic imaging apparatus, and sends a first command to the first radiographic imaging apparatus instructing it to conduct the subsequent radiographing order item.

3 Claims, 12 Drawing Sheets

(52) U.S. Cl.
CPC .......... *A61B 6/4494* (2013.01); *A61B 6/545* (2013.01); *A61B 6/467* (2013.01); *A61B 6/548* (2013.01)

(56) References Cited

U.S. PATENT DOCUMENTS

| | | | | |
|---|---|---|---|---|
| 2010/0169833 | A1 | 7/2010 | Arima | |
| 2011/0069814 | A1* | 3/2011 | Yonekawa | A61B 6/00 378/62 |
| 2012/0321043 | A1* | 12/2012 | Yonekawa | A61B 6/00 378/62 |
| 2012/0321044 | A1* | 12/2012 | Yonekawa | A61B 6/00 378/62 |
| 2013/0038738 | A1* | 2/2013 | Ando | A61B 6/4266 348/162 |
| 2014/0112443 | A1* | 4/2014 | Yonekawa | A61B 6/00 378/62 |
| 2014/0241503 | A1* | 8/2014 | Yonekawa | A61B 6/4233 378/62 |

FOREIGN PATENT DOCUMENTS

| | | | |
|---|---|---|---|
| JP | 2002-191586 | 7/2002 | |
| JP | 2005-003755 | 1/2005 | |
| JP | 2009-172242 | 8/2009 | |
| JP | 2010-148720 | 7/2010 | |
| JP | 2011-104089 | 6/2011 | |
| JP | WO2011142157 A1 * | 11/2011 | .......... A61B 6/4266 |
| JP | 2012-095831 | 5/2012 | |
| JP | 2012-095882 | 5/2012 | |
| JP | 2012-100797 | 5/2012 | |
| WO | WO 2011/142157 | 2/2011 | |
| WO | WO 2011/142157 | 11/2011 | |
| WO | WO 2012/165171 | 12/2012 | |

OTHER PUBLICATIONS

Office Action dated Dec. 16, 2016 which issued in the corresponding Chinese Patent Application No. 201510026653.1.

* cited by examiner

FIG. 7

| RADIOGRAPHING ORDER ID | PATIENT ID | NAME | SEX | AGE | MEDICAL DEPARTMENT | RADIOGRA-PHED SITE | RADIOGRAPHING DIRECTION | BUCKY ID | FPD SIZE |
|---|---|---|---|---|---|---|---|---|---|
| 001 | 100085 | A | MALE | 25 | ORTHOPEDICS | ABDOMEN | FRONT P→A | 002 | 14×17 |
| 002 | 100085 | A | MALE | 25 | ORTHOPEDICS | CHEST | FRONT P→A | 001 | 14×17 |
| 003 | 100085 | A | MALE | 25 | ORTHOPEDICS | NECK | L | 000 | 11×14 |
| 004 | 100085 | A | MALE | 25 | ORTHOPEDICS | UPPER ARM | L | 000 | 10×12 |

ENTER RADIOGRAPHING ORDER INFORMATION OF RADIOGRAPHING TO BE CONDUCTED

| RADIOGRAPHING ORDER ID | PATIENT ID | NAME | SEX | AGE | MEDICAL DEPARTMENT | RADIOGRA-PHED SITE | RADIOGRAPH-ING DIRECTION | BUCKY ID | FPD SIZE |
|---|---|---|---|---|---|---|---|---|---|
| 001 | 100085 | A | MALE | 25 | ORTHOPEDICS | ABDOMEN | FRONT P→A | 002 | 14×17 |
| 002 | 100085 | A | MALE | 25 | ORTHOPEDICS | CHEST | FRONT P→A | 001 | 14×17 |
| 003 | 100085 | A | MALE | 25 | ORTHOPEDICS | NECK | L | 000 | 11×14 |
| 004 | 100085 | A | MALE | 25 | ORTHOPEDICS | UPPER ARM | L | 000 | 10×12 |

P1, P2, P3, P4, P5, P6, P7, P8, P9, P10

ENTER — h13
RETURN — h14

ENTER RADIOGRAPHING ORDER INFORMATION OF RADIOGRAPHING TO BE CONDUCTED

| RADIOGRAPHING ORDER ID | PATIENT ID | NAME | SEX | AGE | MEDICAL DEPARTMENT | RADIOGRA- PHED SITE | RADIOGRAPH- ING DIRECTION | BUCKY ID | FPD SIZE |
|---|---|---|---|---|---|---|---|---|---|
| 001 | 100085 | A | MALE | 25 | ORTHOPEDICS | ABDOMEN | FRONT P→A | 002 | 14×17 |
| 002 | 100085 | A | MALE | 25 | ORTHOPEDICS | CHEST | FRONT P→A | 001 | 14×17 |
| 003 | 100085 | A | MALE | 25 | ORTHOPEDICS | NECK | L | 000 | 10×12 |
| 004 | 100085 | A | MALE | 25 | ORTHOPEDICS | UPPER ARM | L | 000 | 10×12 |

ENTER    RETURN

RADIOGRAPHIC IMAGING SYSTEM

This application is a divisional of U.S. Ser. No. 14/600,876 filed Jan. 20, 2015 which claims priority of Japanese Patent Application No. 2014-010186 filed on Jan. 23, 2014, the entire content of which is hereby incorporated by reference.

BACKGROUND OF THE INVENTION

Field of the Invention

The present invention relates to a radiographic imaging system.

Description of the Related Art

Radiographic images captured by using radiation typified by X-ray images are widely used for the purpose of disease diagnosis and the like. Such medical radiographic images have been captured by using screen films, but computed radiography (CR) apparatuses using photostimulable phosphor sheets are then developed for digitization of radiographic images, and radiographic imaging apparatuses configured to detect emitted radiation by radiation detecting elements and acquire the radiation as digital image data are developed.

Radiographic imaging apparatuses of this type are known as flat panel detectors (FPD) and have been developed as what is called special-purpose machines (also called fixed type apparatuses or the like). In recent years, portable type (also called cassette type or the like) radiographic imaging apparatuses that are made portable by accommodating radiation detecting elements and the like in housings are developed and in practical use.

When the body of a patient that is a subject is radiographed in a facility such as a hospital by using such a special-purpose or portable radiographic imaging apparatus, a radiographic imaging system in which the special-purpose radiographic imaging apparatus is installed in a radiography room in the facility or the portable radiographic imaging apparatus is brought in a radiography room and radiographing is carried out by controlling the radiographic imaging apparatus radiation generating apparatus and the like by a console installed outside of the radiography room may be built.

Such a radiographic imaging system is usually built so that radiographic imaging is carried out on the basis of radiographing order information shown in FIG. 7, which will be described later, for example. The radiographing order information specifies information, instructions and the like on radiographic imaging determined on the basis of questioning of a patient, and specifies and registers items including patient information such as a patient ID, the site of the body of the patient to be radiographed (that is, the site to be radiographed), and radiographing conditions such as the radiographing direction and the size of the radiographic imaging apparatus (FPD) to be used for imaging, for example. The configuration and the like of the radiographing order information will be described later.

A console manages the radiographing order information on radiographic imaging to be conducted on a day by acquiring and selecting the radiographing order information, and when a radiographic image (also referred to as an image for providing diagnosis or the like) generated on the basis of the image data and the like transmitted from the radiographic imaging apparatus is approved by an operator such as a radiological technologist after radiographic imaging, the console associates the radiographic image with the radiographing order information to perform a determination process.

Since radiographing is conducted focusing on the radiographing order information in this manner, radiographic imaging systems configured to display, on the screen of a console, icons I1 to I4, etc. associated with radiographing order information items on radiographing to be conducted, for example, so that an operator such as a radiological technologist can easily and properly conduct radiographing by operating icons and the like by using the console are developed in recent years as shown in FIG. 9, for example, which will be described later (refer to WO 2011/142157 A1, for example).

In particular, WO 2011/142157 A1 discloses a radiographic imaging system in which a console selects radiographing order information specifying radiographing conditions under which radiographic imaging can be conducted with the smallest degree of change of a current state of a special-purpose or portable radiographic imaging apparatus, a radiation source of a radiation generating apparatus and the like present in a radiography room, for example, on the basis of the current state, that is, the radiographic imaging apparatus being in operation, the direction of the radiation source, and the like. Furthermore, an icon associated with the radiographing order information is displayed in a manner different from the other icons (hereinafter referred to as focused display) by displaying the icon with a predetermined color, or displayed with a border of a predetermined color so that the icon will be highlighted as shown in FIG. 9, which will be described later. The process described above is repeated each time radiographing is completed, and the focused display is automatically switched each time radiographing is completed.

According to the radiographic imaging system, the operator such as a radiological technologist can efficiently conduct radiographing by conducting radiographing according to the switched focused display, and the radiographic imaging system is easy to use for the operator. Refer to WO 2011/142157 A1 for details of such a radiographic imaging system.

Furthermore, in the radiographic imaging system disclosed in WO 2011/142157 A1, when the operator such as a radiological technologist clicks an icon different from an icon displayed in a focused manner as a result of automatic determination by the console as described above, for example, for conducting radiographing different from radiographing associated with the icon displayed in a focused manner, the console is configured to give priority to the intention of the operator, switch the focused display to the icon clicked by the operator and control the radiation generating apparatus to conduct radiographing relating to the radiographing order information associated with the icon.

In addition to the operation by the console as described above, when the operator such as a radiological technologist presses a power switch or a selection switch (see 37 and 38 in FIG. 2, which will be described later) of any of radiographic imaging apparatuses in a radiography room and if the selected radiographic imaging apparatus is different from the radiographic imaging apparatus specified by the radiographing order information associated with the icon displayed in a focused manner, the console is configured to give priority to the intention of the operator, determine that the radiographic imaging apparatus whose power switch or selection switch is pressed is a radiographic imaging apparatus to be used for radiographing to be conducted next, and switches the focused display to the icon associated with the radiographing order information specifying the radiographic imaging apparatus.

With such a configuration, the radiographic imaging system is also easy to use for the operator in that priority is given to the intention of the operator such as a radiological technologist and the icon to be displayed in a focused manner (that is, the radiographing order information associated with the icon) can be properly changed according to the intention.

When radiographing is conducted multiple times by such a radiographic imaging system, a radiographic image generated from image data obtained by radiographing needs to be reliably associated with the radiographing order information of the radiographing. In other words, configuration is required to be such that a radiographic image generated as a result of certain radiographing will not be associated with radiographing order information different from the radiographing order information of the radiographing.

With the radiographic imaging system disclosed in WO 2011/142157 A1 described above, however, it is found that the following problem may be caused. Specifically, as shown in FIG. 9 to be described later, for example, when the operator such as a radiological technologist moves into the radiography room and presses a power switch or a selection switch of a radiographic imaging apparatus having a size of 10×12 inches, for example to conduct radiographing of the neck of a patient (that is, radiographing associated with an icon I3 in FIG. 9) in a state in which icons I1 to I4 associated with selected radiographing order information items (see FIG. 7 to be described later) are displayed on a screen of the console, an ID "FPD-002" that is identification information of the radiographic imaging apparatus is transmitted from the radiographic imaging apparatus to the console.

Upon receiving the information, the console determines that the operator such as a radiological technologist has not selected radiographing associated with the icon I3 that is displayed in a focused manner (radiographing using the radiographic imaging apparatus of 11×14 inches) but has selected radiographing associated with the icon I4 using the radiographic imaging apparatus of 10×12 inches since the size of the radiographic imaging apparatus with "FPD-002" is 10×12 inches, and switches the focused display to the icon I4 to give priority to the intention of the operator.

Thus, although the operator such as a radiological technologist intends to conduct radiographing associated with the icon I3 for radiographing the "neck" of the patient by using the radiographic imaging apparatus of 10×12 inches, the console determines that radiographing associated with the icon I4 for radiographing an "upper arm" of the patient is to be conducted and switches the focused display to the icon I4. If the operator conducts radiographing by applying the radiographic imaging apparatus to the neck of the patient without noticing the above, the console generates a radiographic image on the basis of image data, etc. transmitted from the radiographic imaging apparatus but associates the radiographic image of the "neck" with the radiographing order information associated with the icon I4, that is, the radiographing order information specifying radiographing of the "upper arm" of the patient.

It is found that a radiographic image generated by conducting radiographing may be associated with radiographing order information (the radiographing order information associated with the icon I4 in the example above) different from the radiographing order information (the radiographing order information associated with the icon I3 in the example above) on the radiographing as described above. This situation is not necessarily a peculiar situation but a perfectly possible situation during normal radiographing operation.

Specifically, the aforementioned situation may occur in such a case where the operator such as a radiological technologist uses a radiographic imaging apparatus of 10×12 inches by mistake although the radiographing order information associated with the icon I3 specifies 11×14 inches as the size of the radiographic imaging apparatus to be used and the size "11×14 inches" is displayed on the icon I3, for example.

In addition, the aforementioned situation may also occur in such a case where the size of the radiographic imaging apparatus to be used for radiographing the "neck" of a patient is registered in radiographing order information as "11×14" by mistake although the radiographic imaging apparatus of 10×12 inches is intended to be used therefor in generating the radiographing order information in advance and the operator uses the radiographic imaging apparatus of 10×12 inches without noticing that "11×14" is incorrectly displayed on the icon I3, for example.

Furthermore, the aforementioned situation may also occur in such a case where the operator is aware that the radiographing order information associated with the icon I3 specifies to use the radiographic imaging apparatus of 11×14 inches but determines that the size 11×14 inches is too large at the point of actually using the radiographic imaging apparatus or cannot help using the radiographic imaging apparatus of 10×12 inches owing to a dead battery of the radiographic imaging apparatus of 11×14 inches, for example. Furthermore, in such a case where the size of a focused grid provided in a radiography room does not match with that of the radiographic imaging apparatus that is originally planned to be used and it is difficult to position the focused grid on the radiographic imaging apparatus, the size of the radiographic imaging apparatus may be changed to match with that of the focused grid.

Furthermore, the aforementioned situation may also occur in such a case where the operator such as a radiological technologist intends to change the scintillator type of the radiographic imaging apparatus from a radiographic imaging apparatus (having a size of 11×14 inches) having a CsI columnar crystal scintillator to a radiographic imaging apparatus (having a size of 10×12 inches) having a GOS ($Gd_2O_2S$) layered scintillator, for example.

As described above, it is common for operators such as radiological technologists to change a radiographic imaging apparatus to be used for radiographing to another radiographic imaging apparatus in normal radiographing operation. It is, however, necessary to avoid such a situation in which a radiographic image is generated by the console after radiographing (radiographing associated with the icon I3 in the example above) is conducted but the radiographic image is associated with radiographing order information (radiographing order information associated with the icon I4) different from that on the radiographing by mistake as described above as a result of changing the radiographic imaging apparatus to be used in this manner.

Such a mistake is caused because switching of focused display of icons takes place in such a manner that is not intended by an operator such as a radiological technologist and without being noticed by the operator. In other words, this is caused because the console switches radiographing order information specified for radiographing to be conducted next to different radiographing order information without being noticed by an operator such as a radiological technologist.

SUMMARY OF THE INVENTION

The present invention has been made in view of the aforementioned drawbacks, and an object thereof is to provide a radiographic imaging system capable of prevent a console from switching radiographing order information specified for radiographing to be conducted next to different radiographing order information in such a manner that is not intended by an operator (user) such as a radiological technologist and correctly associating a generated radiographic image with radiographing order information.

To achieve the abovementioned object, one aspect of the invention is directed to A radiographic imaging system comprising an x-ray radiation source configured to irradiate a subject with radiation; multiple radiographic imaging apparatuses each including multiple radiation detecting elements arranged two-dimensionally, and configured to read charges generated in the radiation detecting elements as a result of irradiation with radiation as image data and transmit an image signal in response to a command; and a console structured to communicate with, to control with a command the operation of, and to receive image signals from, the multiple radiographic imaging apparatuses and configured to acquire multiple radiographing order information items indicating which of the multiple radiographic imaging apparatuses is to be used for conducting radiographing, the console being configured so that, upon receiving the image signal from a first of the radiographic imaging apparatuses, the console determines from the multiple radiographing order information items a subsequent radiographing order item to be conducted by the first radiographic imaging apparatus, and sends a first command to the first radiographic imaging apparatus instructing the first radiographic imaging apparatus to conduct the subsequent radiographing order item.

Another aspect of the invention is directed to a radiographic imaging system reflecting one aspect of the present invention comprises: a radiation source configured to irradiate a subject with radiation; multiple radiographic imaging apparatuses each including multiple radiation detecting elements arranged two-dimensionally, and configured to read charges generated in the radiation detecting elements as a result of irradiation with radiation as image data and transmit a signal in response to user's operation; and a console configured to register multiple radiographing order information items each including information indicating which of the multiple radiographic imaging apparatuses is to be used for conducting radiographing, or acquire the registered multiple radiographing order information items, wherein upon receiving the signal from one of the radiographic imaging apparatuses, the console changes specification of information on the radiographic imaging apparatus in the radiographing order information item determined for radiographing to be conducted next to information on the radiographic imaging apparatus from which the signal is received without switching the radiographing order information item to another radiographing order information item.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 7 is a table showing an example configuration of radiographing order information;

FIG. 8 is a diagram showing an example of a selection screen displaying the radiographing order information;

FIG. 10 is a diagram showing radiographing order information in a state in which an "FPD size" is changed from the state of FIG. 8;

DESCRIPTION OF THE PREFERRED EMBODIMENTS

Hereinafter, a radiographic imaging system according to an embodiment of the present invention will be described with reference to the drawings. However, the scope of the invention is not limited to the illustrated examples.

In the following, what is called an indirect radiographic imaging apparatus having a scintillator and the like and configured to convert emitted radiation to light having a different wavelength such as visible light to obtain an electrical signal will be described as a radiographic imaging apparatus used in the radiographic imaging system, but the present invention can also be applied to what is called a direct radiographic imaging apparatus configured to detect radiation directly using a radiation detecting element without a scintillator or the like. Furthermore, although a case in which the radiographic imaging apparatus is portable will be described, the present invention can also be applied to a special-purpose radiographic imaging apparatus as described above. Furthermore, the present invention is not limited to shown examples presented below.

[Regarding Configuration, etc. of Radiographic Imaging System]

Figure 1:
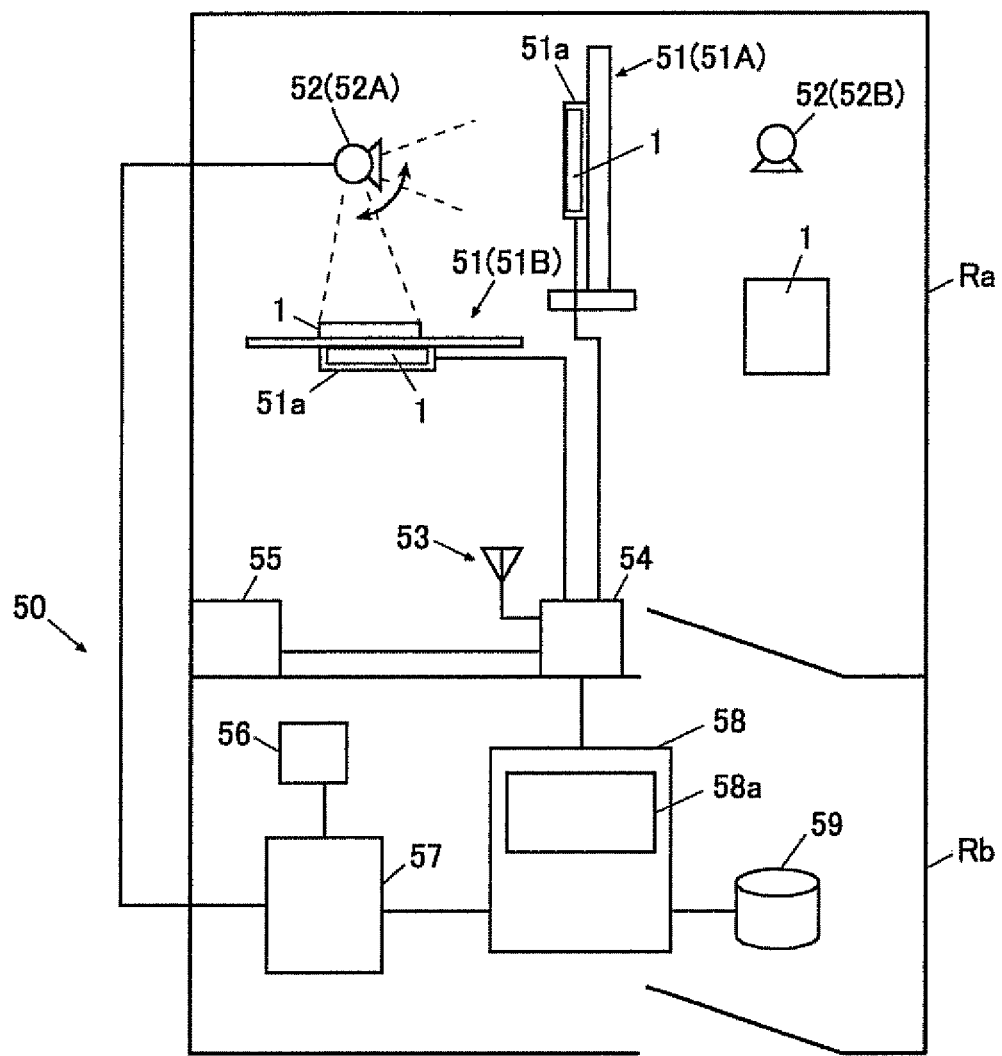
FIG. 1 is a diagram showing an overall configuration of a radiographic imaging system according to an embodiment.

FIG. 1 is a diagram showing a basic configuration of a radiographic imaging system according to the present embodiment. Although a case in which a radiography room Ra and a console 58 are associated in one-to-one correspondence with each other is shown in FIG. 1, the present invention can also be applied to a radiographic imaging system in which multiple radiography rooms Ra and a single or multiple consoles 58 are connected via a network or the like, for example, which is not shown. For example, the present invention can also be applied to such a case in which one radiological technologist or the like selects multiple radiographing order information items by using one console and sequentially conduct radiographing according to the multiple radiographing order information items by using multiple radiography rooms.

A radiography room Ra is a room for irradiating a subject that is part of the body of a patient (that is, a site of a patient to be radiographed) with radiation to radiographing the subject, and has installed therein a radiation source 52 or the like for a radiation generating apparatus 57 for irradiating a subject with radiation. The radiography room Ra is shielded with zinc or the like to prevent leakage of radiation to outside of the room.

[Regarding Radiographic Imaging Apparatus]

Figure 2:
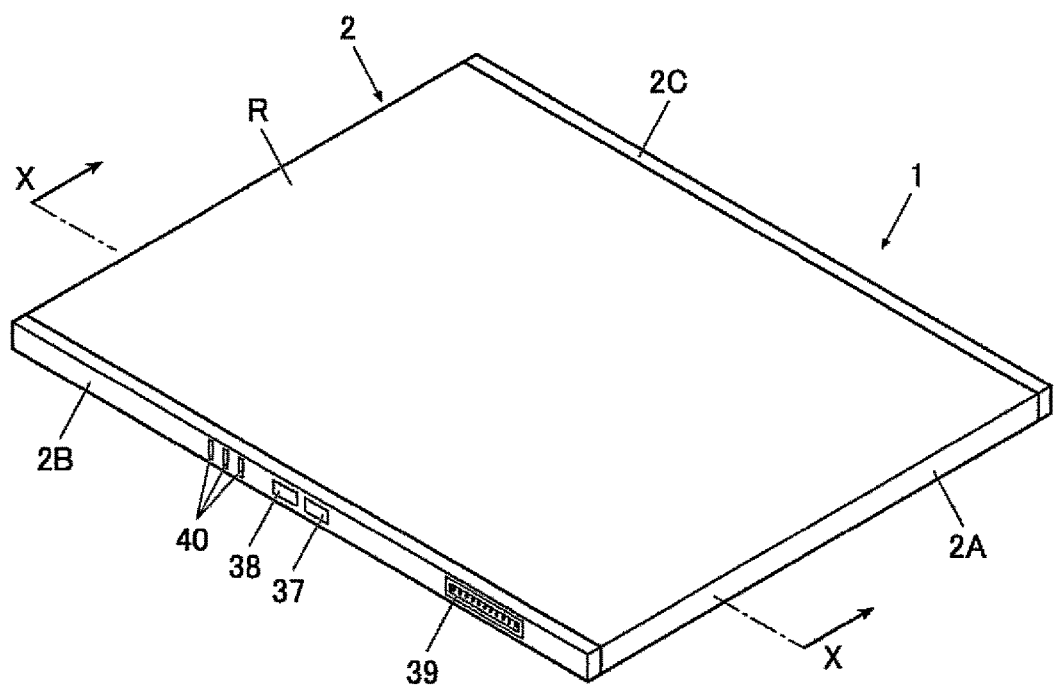
FIG. 2 is a perspective view of an external appearance of a radiographic imaging apparatus.
Figure 3:
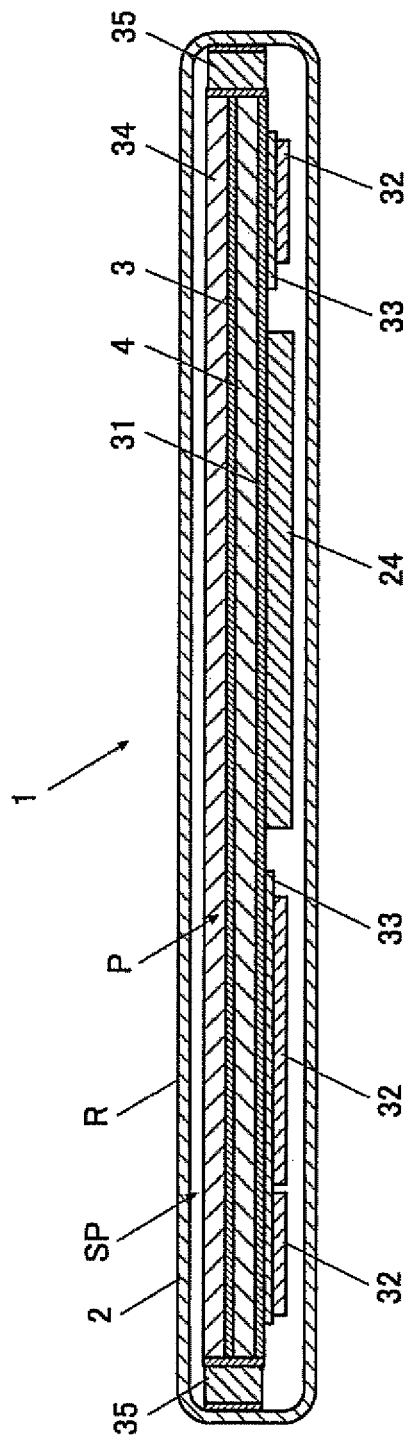
FIG. 3 is a cross-sectional view taken along line X-X in FIG. 2.

Here, a radiographic imaging apparatus 1 used for radiographic imaging in a radiographic imaging system 50 will be described. FIG. 2 is a perspective view of an external appearance of the radiographic imaging apparatus, and FIG. 3 is a cross-sectional view taken along line X-X in FIG. 2. Note that the relative sizes of respective components in FIGS. 2, 3, etc. do not necessarily reflect the actual relative sizes.

As shown in FIGS. 2 and 3, the radiographic imaging apparatus 1 includes a sensor panel SP including a scintillator 3, a sensor board 4, etc. accommodated in a housing 2 having a radiation incident surface R. One cover member 2B of the housing 2 is provided with a power switch 37, a selection switch 38, a connector 39, an indicator 40 including LEDs or the like for indicating a battery condition, an operating condition of the radiographic imaging apparatus 1, etc., and the like. In addition, a cover member 2C, etc., on the opposite side of the housing 2 is provided with an antenna device 41 (see FIG. 5, which will be described later) that is a communication unit for wirelessly transmitting image data D, etc. to the console 58 (see FIG. 1), which will be described later, and that is embedded or arranged in a certain manner. Alternatively, a cable that is not shown can be attached to the connector 39 to transmit the image data D, etc., to the console 58 in a wired manner.

As shown in FIG. 3, a base 31 is provided in the housing 2, and the sensor board 4 is provided on the side of radiation incident surface R of the base 31 (hereinafter simply referred to as the upper surface side according to the vertical direction in FIG. 3) with a zinc thin sheet or the like, which is not shown, therebetween. A scintillator board 34 is provided so that a scintillator 3 configured to convert emitted radiation to light such as visible light is arranged on the upper face side of the sensor board 4. In addition, A PCB 33 on which electronic components 32, etc. are arranged, a battery 24, etc. are mounted on the lower surface side of the base 31. The sensor panel SP is formed by the base 31, the sensor board 4, etc. in this manner. In the present embodiment, a shock absorber 35 is provided between the sensor panel SP and the housing 2.

Figure 4:
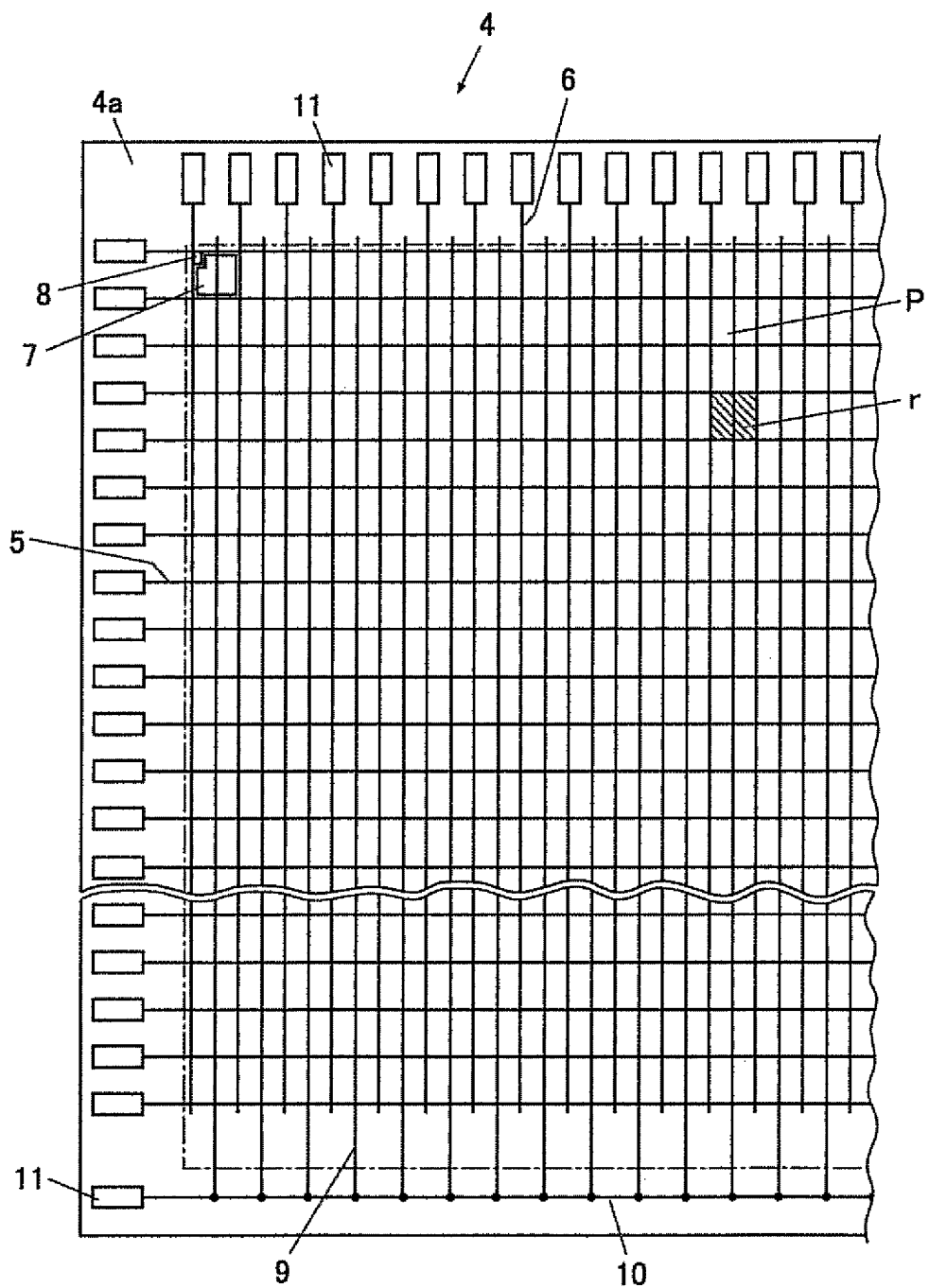
FIG. 4 is a plan view showing a configuration of a sensor board of the radiographic imaging apparatus.

As shown in FIG. 4, multiple scanning lines 5 and multiple signal lines 6 arranged in such a manner that the lines intersect one another on a surface 4a of the sensor board 4 on the side opposite to the scintillator 3. Furthermore, a radiation detecting element 7 is provided in each of small regions r defined by the multiple scanning lines 5 and the multiple signal lines 6 on the surface 4a of the sensor board 4. Thus, the radiation detecting elements 7 are arranged two-dimensionally on the sensor board 4. Although photodiodes are used for the radiation detecting elements 7 in the present embodiment, phototransistors or the like may be used, for example.

The radiation detecting elements 7 are connected to the signal lines 6 via thin film transistors (hereinafter referred to as TFTs) 8 that are switch elements, and the signal lines 6 are each connected to a readout circuit, which is not shown. The radiation detecting elements 7 are configured such that charges are generated therein in an amount corresponding to the amount of emitted radiation (visible light obtained by converting emitted radiation by the scintillator 3 in the present embodiment) and that the charges flow from the radiation detecting elements 7 to the readout circuits via the signal lines 6 and the TFTs 8 and are converted into the image data D by the readout circuits when the TFTs 8 are turned on in a process of reading the image data D. In the present embodiment, charges generated in the radiation detecting elements 7 as a result of emission of radiation are read out as the image data D in this manner.

Note that an area P (that is, an area P inside of a dashed-dotted line in FIG. 4) in which the radiation detecting elements 7 are arranged corresponds to a detecting unit in the present embodiment. Furthermore, the radiation detecting elements 7 are connected with bias lines 9, which are connected to a connection line 10. A reverse bias voltage is applied to the radiation detecting elements 7 from a bias supply, which is not shown, via the bias lines 9 and the connection line 10. In addition, the scanning lines 5, the signal lines 6, the connection line 10 of the bias lines 9, etc. are connected to input/output terminals 11, and connected to the readout circuits, the electronic components 32, etc. described above via the input/output terminals 11.

In the present embodiment, upon reading the image data D from the radiation detecting elements 7 as described above, the radiographic imaging apparatus 1 is configured to perform a process of reading out offset data O in a similar manner but in a state in which radiation is not emitted and transmit the read image data D, offset data O, etc. to the console 58 in a wireless or wired manner. Part of the read image data D may be extracted as preview image data Dp and the preview image data Dp may be transmitted to the console 58 prior to transmission of the image data D, etc.

[Regarding Other Apparatuses in Radiographic Imaging System]

Next, apparatuses, etc. in the radiographic imaging system 50 will be described. As shown in FIG. 1, a bucky apparatus 51 can be used with the portable radiographic imaging apparatus 1 mounted on a cassette holding unit (also referred to as a cassette holder) 51a. Although a bucky apparatus 51A for radiographing in a standing position and a bucky apparatus 51B for radiographing in a recumbent position are provided as the bucky apparatus 51 in the radiography room Ra in the present embodiment as shown in FIG. 1, the present invention is not limited to such a case where both of bucky apparatuses 51A and 51B for radiographing in a standing position and in a recumbent position are provided.

Figure 5:
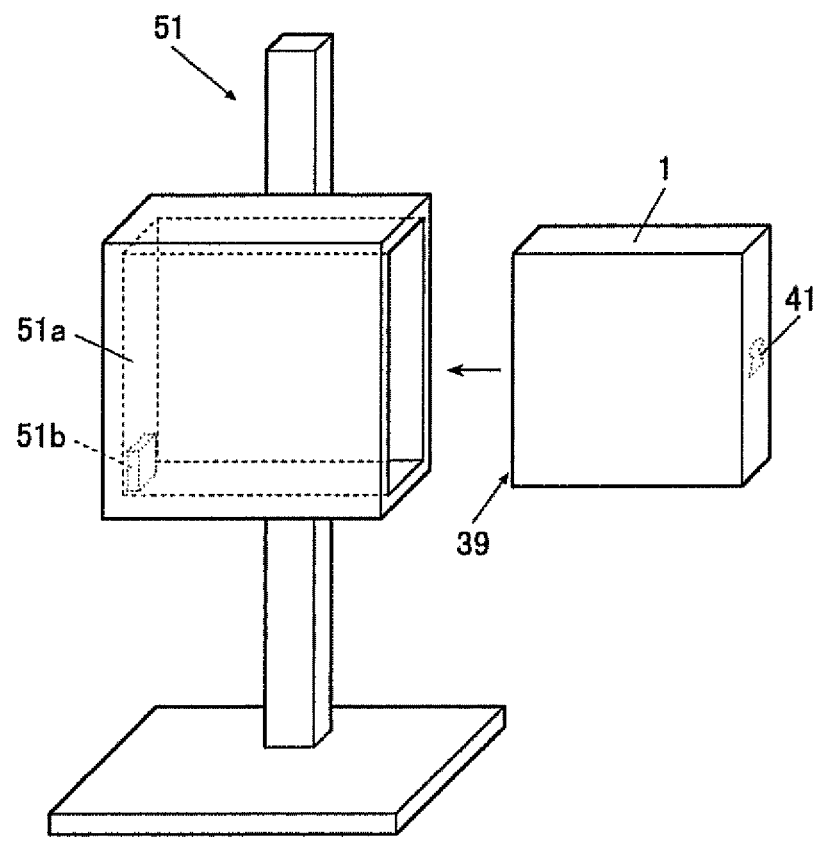
FIG. 5 is a view explaining a bucky apparatus in which a connector is provided inside of a cassette holding unit.

As shown in FIG. 5, a connector 51b to be connected to the connector 39 (see FIG. 2) of the mounted radiographic imaging apparatus 1 may be provided inside of the cassette holding unit 51a of the bucky apparatus 51, for example. Although a case of the bucky apparatus 51A for radiographing in a standing position is shown in FIG. 5, the same applies to the bucky apparatus 51B for radiographing in a recumbent position.

Alternatively, instead of providing the connector 51b inside of the cassette holding unit 51a of the bucky apparatus 51, a connector of a cable extending from the bucky apparatus 51 may be connected to the connector 39 of the radiographic imaging apparatus 1 before mounting the radiographic imaging apparatus 1 on the bucky apparatus 51 and the radiographic imaging apparatus 1 may be mounted on the cassette holding unit 51a of the bucky apparatus 51 in this state, which is not shown. In this case, power may be supplied to the radiographic imaging apparatus 1 from an external power source via the cable, for example, so that the battery 24 of the radiographic imaging apparatus 1 is not used, which allows continuous radiographing without concern for lowering battery in continuous radiographing of front chests, etc. in a mass examination or the like.

Furthermore, in the present embodiment, when the connector 51b and the connector 39 of the radiographic imaging apparatus 1 are connected, the bucky apparatus 51 is configured to read a cassette ID that is identification information of the radiographic imaging apparatus 1 from the radiographic imaging apparatus 1 and transmits the cassette ID of the radiographic imaging apparatus 1 in association with a bucky ID that is identification information of the bucky apparatus 51 to the console 58.

As shown in FIG. 1, at least one radiation source 52 of the radiation generating apparatus 57 for irradiating a subject with radiation is provided in the radiography room Ra. In the present embodiment, one radiation source 52A of the radiation sources 52 is suspended from the ceiling of the radiography room Ra, and is configured to be turned on on the basis of an instruction from the console 58 for radiographing and moved to a predetermined position by a moving unit, which is not shown. Radiation can be emitted to the radiographic imaging apparatus 1 mounted on the bucky apparatus 51A for radiographing in a standing position and the bucky apparatus 51B for radiographing in a recumbent position from one radiation source 52 by changing the radiation emitting direction, the position, etc. of the radiation source 52. Alternatively, a radiation source 52 may be provided for each of the bucky apparatus 51A for radiographing in a standing position and the bucky apparatus 51B for radiographing in a recumbent position.

Furthermore, as shown in FIG. 1, a portable radiation source 52B may be brought into the radiography room Ra for radiographing. Radiographing can thus be conducted by emitting radiation from the portable radiation source 52B in a state in which the radiographic imaging apparatus 1 is applied to a site of the body of a patient that is a subject without mounting the radiographic imaging apparatus 1 on the bucky apparatus 51, that is, in a stand-alone state.

As shown in FIG. 1, a relay (also referred to as a base station) 54 including an access point 53 for relaying communication between apparatuses such as the radiographic imaging apparatus 1 in the radiography room Ra and apparatuses such as the console 58 outside of the radiography room Ra in a wireless or wired manner is provided in the radiography room Ra. The relay 54 includes a converter, which is not shown, configured to convert a signal or the like for communication via a local area network (LAN) to be transmitted to the radiation generating apparatus 57 from the radiographic imaging apparatus 1, the console 58, etc. into a signal or the like for the radiation generating apparatus 57, and vice versa.

Figure 6:
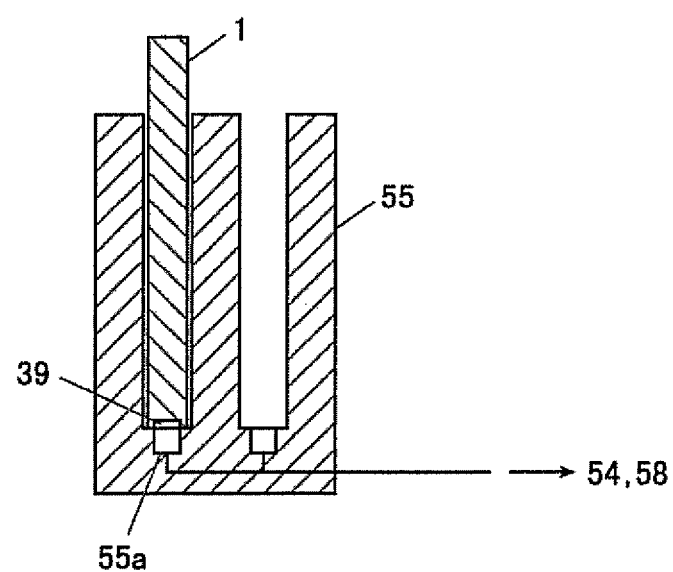
FIG. 6 is a cross-sectional view showing a state in which the radiographic imaging apparatus is inserted in a cradle and connectors are connected to each other.

In the present embodiment, the relay 54 is connected with a cradle 55. As shown in FIG. 6, when the radiographic imaging apparatus 1 brought into the radiography room Ra is inserted in the cradle 55 so that the connector 39 of the radiographic imaging apparatus 1 and a connector 55a of the cradle 55 are connected, the radiographic imaging apparatus 1 is configured to notify the relay 54 of the cassette ID via the cradle 55. When the cassette ID of the radiographic imaging apparatus 1 is transmitted from the cradle 55, the relay 54 then notifies the console 58 of the cassette ID.

Note that the cradle 55 may be configured to store and charge the radiographic imaging apparatus 1. Furthermore, although the cradle 55 having two insertion ports for inserting the radiographic imaging apparatus 1 is shown in FIG. 6, the number of insertion ports may be one or three or more. Furthermore, the cradle 55 may be installed in either of the radiography room Ra and an anteroom Rb. When the cradle 55 is installed in the radiography room Ra, the cradle 55 is arranged at a position that radiation emitted from the radiation source 52 does not reach, such as a corner position in the radiography room Ra.

Furthermore, although not shown, a tag reader that is a detecting unit for detecting the radiographic imaging apparatus 1 brought into the radiography room Ra or the anteroom Rb and notifying the console 58 of the cassette ID may be provided near the door of the anteroom Rb (see FIG. 1), for example, instead of using the cradle 55 as in the present embodiment. In this case, a tag, which is not shown, such as a radio frequency identification (RFID) tag is contained in advance in the radiographic imaging apparatus 1 and unique information such as the cassette ID of the radiographic imaging apparatus 1 is stored in the tag. The tag reader may be configured to read information such as the cassette ID from the tag of the radiographic imaging apparatus 1 when the radiographic imaging apparatus 1 is brought into the radiography room Ra or the anteroom Rb passing near the tag reader, and notify the console 58 of the cassette ID.

As shown in FIG. 1, the radiation generating apparatus 57 having an exposure switch 56 or the like for instructing the radiation source 52 to start emission of radiation is provided in the anteroom (also referred to as an operation room) Rb. When a tube voltage, a tube current, an emission time, etc. are set, the radiation generating apparatus 57 is configured to supply the set tube voltage and tube current to the radiation source 52 to start the radiation source 52 and emit radiation in an amount corresponding to the tube voltage, etc. for the set emission time from the radiation source 52. The tube voltage, etc. to be applied to the radiation generating apparatus can be set on an operator console 57 of the radiation generating apparatus, but can also be set on the console 58 in the present embodiment.

The console 58 is provided in the anteroom Rb in the present embodiment, and is a computer or the like in which a central processing unit (CPU), a read only memory (ROM), a random access memory (RAM), an input/output interface, etc. are connected to a bus, which are not shown. The ROM stores predetermined programs, and the console 58 is configured to read and expand necessary programs in a work area of the RAM to execute various processes according to the programs. The console 58 may be a dedicated device, for example, instead of a general-purpose computer.

The console 58 is provided with a display unit 58a that is a cathode ray tube (CRT), a liquid crystal display (LCD), or the like and connected with an input unit such as a keyboard and a mouse which is not shown. The console 58 is also connected with a storage unit 59 that is a hard disk or the like, and also with external devices, which are not shown, such as other computers and an imager configured to record and output radiographic images on an image recording medium such as a film on the basis of the image data D output from the console 58 via a local area network (LAN) or the like. Furthermore, the console 58 is connected with a hospital information system (HIS) and a radiology information system (RIS), which will be described later, via a network.

[Regarding Typical Processes of Console 58]

Next, typical processes of the console 58 according to the present embodiment will be described. Processes of the console 58 unique to the present invention will be described later.

In the present embodiment, when the radiographic imaging apparatus 1 brought into the radiography room Ra is inserted in the cradle 55 and the cassette ID or the like of the radiographic imaging apparatus 1 is transmitted via the relay 54 as described above, the console 58 is configured to save the cassette ID or the like in the storage unit 59, recognizes that the radiographic imaging apparatus 1 having the cassette ID is brought into the radiography room Ra or the anteroom Rb, and manages the radiographic imaging apparatus 1.

In addition, when the cassette ID of the radiographic imaging apparatus 1 and the bucky ID are transmitted from the bucky apparatus 51 having the connector 51b to which the radiographic imaging apparatus 1 is connected as described above, the console 58 saves the cassette ID saved in the storage unit 59 in association with the bucky ID. In this manner, the console 58 recognizes that the radiographic imaging apparatus 1 having the cassette ID is mounted on the bucky apparatus 51 having the bucky ID in the radiography room Ra and manages the radiographic imaging apparatus 1. When the radiographic imaging apparatus 1 and the connector 51b of the bucky apparatus 51 are disconnected from each other, the console 58 disassociates the cassette ID of the radiographic imaging apparatus 1 saved in the storage unit 59 from the bucky ID and saves only the cassette ID. In this manner, the console 58 recognizes that the radiographic imaging apparatus 1 having the cassette ID is in a stand-alone state without being mounted on the bucky apparatus 51 and manages the radiographic imaging apparatus 1.

Furthermore, in the present embodiment, when the power switch 37 of the radiographic imaging apparatus 1 is turned on or off, an ON signal indicating that the power supply is turned on or an OFF signal indicating that the power supply is turned off is transmitted with the cassette ID of the radiographic imaging apparatus 1 to the console 58 from the radiographic imaging apparatus 1. When the signal and the cassette ID are transmitted, the console 58 saves the cassette ID saved in the storage unit 59 in association with information on the state (that is, "ON" or "OFF") of the power supply of the radiographic imaging apparatus 1. In this manner, the console 58 recognizes that the power supply of the radiographic imaging apparatus 1 having the cassette ID is ON or OFF and manages the radiographic imaging apparatus 1.

In the present embodiment, the console 58 recognizes and manages the radiographic imaging apparatus 1 brought into the radiography room Ra or the anteroom Rb, recognizes which radiographic imaging apparatus 1 is mounted on the bucky apparatus 51 and manages the radiographic imaging apparatus 1 when the radiographic imaging apparatus 1 is used in a state mounted on the bucky apparatus 51, and recognizes and manages a power consumption mode of each radiographic imaging apparatus 1 as described above. When the radiographic imaging system 50 includes multiple radiography rooms Ra and a single or multiple consoles 58 connected with one another via a network or the like as described above, the management processes described above may be conducted by a management device, which is not shown, such as a server connected to the network instead of conducting the management processes by the console 58.

Furthermore, as described above, the HIS and the RIS, which are not shown, are connected to the console 58 via the network, information on patients, etc. is registered in the HIS, and radiographing order information and the like in which information necessary for conducting predetermined radiographic imaging on individual patients is registered in the RIS.

The radiographing order information includes a "patient ID" P2, the "name" P3, the "sex" P4, the "age" P5, the "medical department" P6, etc., that are patient information, and the "radiographed site" P7, the "radiographing direction" P8, etc. that are radiographing conditions as shown in FIG. 7, for example. In the present embodiment, an item of the "bucky ID" P9 that is information on whether or not radiographing is to be conducted in a state where the radiographic imaging apparatus 1 is mounted on the bucky apparatus 51 is further provided, and the bucky ID is specified when the radiographic imaging apparatus 1 is mounted on the bucky apparatus 51.

In the example shown in FIG. 7, the bucky IDs "001" and "002" represent the bucky apparatus 51A for radiographing in a standing position and the bucky apparatus 51B for radiographing in a recumbent position, respectively, and the bucky ID "000" indicates that the radiographic imaging apparatus 1 is used in a stand-alone state without being mounted on the bucky apparatus 51. Note that drawings representing the bucky apparatus for radiographing in a standing position, the bucky apparatus for radiographing in a recumbent position, and the radiographic imaging apparatus in the stand-alone state, for example, may be entered for specification in the column of the "bucky ID" P9 instead of or in addition to the bucky IDs.

The radiographing order information is further provided with an item of the "FPD size" P10 for specifying the size of the radiographic imaging apparatus (FPD) 1 to be used for the radiographing, and the size such as 17×17 inches (430 mm×430 mm), 14×17 inches (345 mm×430 mm), 14×14 inches (385 mm×390 mm), 11×14 inches (279 mm×354 mm), and 10×12 inches (251 mm×302 mm). In the present embodiment, the "FPD size" P10 that is the size of the radiographic imaging apparatus 1 corresponds to information on the radiographic imaging apparatus in the radiographing order information, and containing this information in the radiographing order information for specification corresponds to specification of information on the radiographic imaging apparatus in the radiographing order information.

Alternatively, colors (such as red, yellow, and blue) or patterns (such as stripes and dots) assigned to the respective sizes in advance, which are not shown, may be entered in the column of the "FPD size" P10 for specification instead of or in addition to the inch sizes described above. In this case, if the colors or patterns different from size to size are displayed on the surfaces opposite to the radiation incident surfaces R (see FIGS. 2 and 3) of radiographic imaging apparatuses 1, for example, there is an advantage that the operator such as a radiological technologist can easily and properly recognize the size of a radiographic imaging apparatus 1 by seeing the color or the pattern thereof.

Note that the scintillator types (such as CsI columnar crystal and GOS layer) described above, for example, may be displayed in a distinguished manner by using the colors and patterns in addition to the sizes of the radiographic imaging apparatuses 1. Specifically, the sizes may be represented by colors and the scintillator types may be represented by patterns, for example, to display the sizes and the scintillator types in a distinguished manner.

Furthermore, in the present embodiment, the "radiographing order IDs" P1 are automatically assigned to the radiographing order information items in the order of registration of radiographing orders as shown in FIG. 7. Note that the details such as patient information and radiographing conditions that can be specified by the radiographing order information are not limited to those described above but may also include information such as the date of birth, the number of consultations, the radiation dose of a patient.

In the present embodiment, the console 58 is configured to acquire necessary radiographing order information, patient information, etc. from the RIS and the HIS when operated by an operator such as a radiological technologist. Alternatively, the radiographing order information may be directly input to and registered in the console 58 by using a special-purpose terminal or the like instead of acquiring the radiographing order information from the RIS. In this case, the radiographing order information may be registered when radiographing is conducted, and when the radiographing order information is registered in advance, the console 58 is configured to acquire a necessary radiographing order information item from the radiographing order information registered in the storage unit 59.

Upon acquiring the radiographing order information (including the case where the radiographing order information is directly input), the console 58 displays a list of radiographing order information items on a selection screen H1 displayed on the display unit 58a (see FIG. 1) as shown in FIG. 8. In the present embodiment, the selection screen H1 is provided with a radiographing order information display field h11 for displaying the list of radiographing order information items and selection buttons h12 for selecting a radiographing order information item of radiographing to be conducted on the left of the radiographing order information display field h11. Furthermore, an enter button h13 and a return button h14 are provided below the radiographing order information display field h11.

Figure 9:
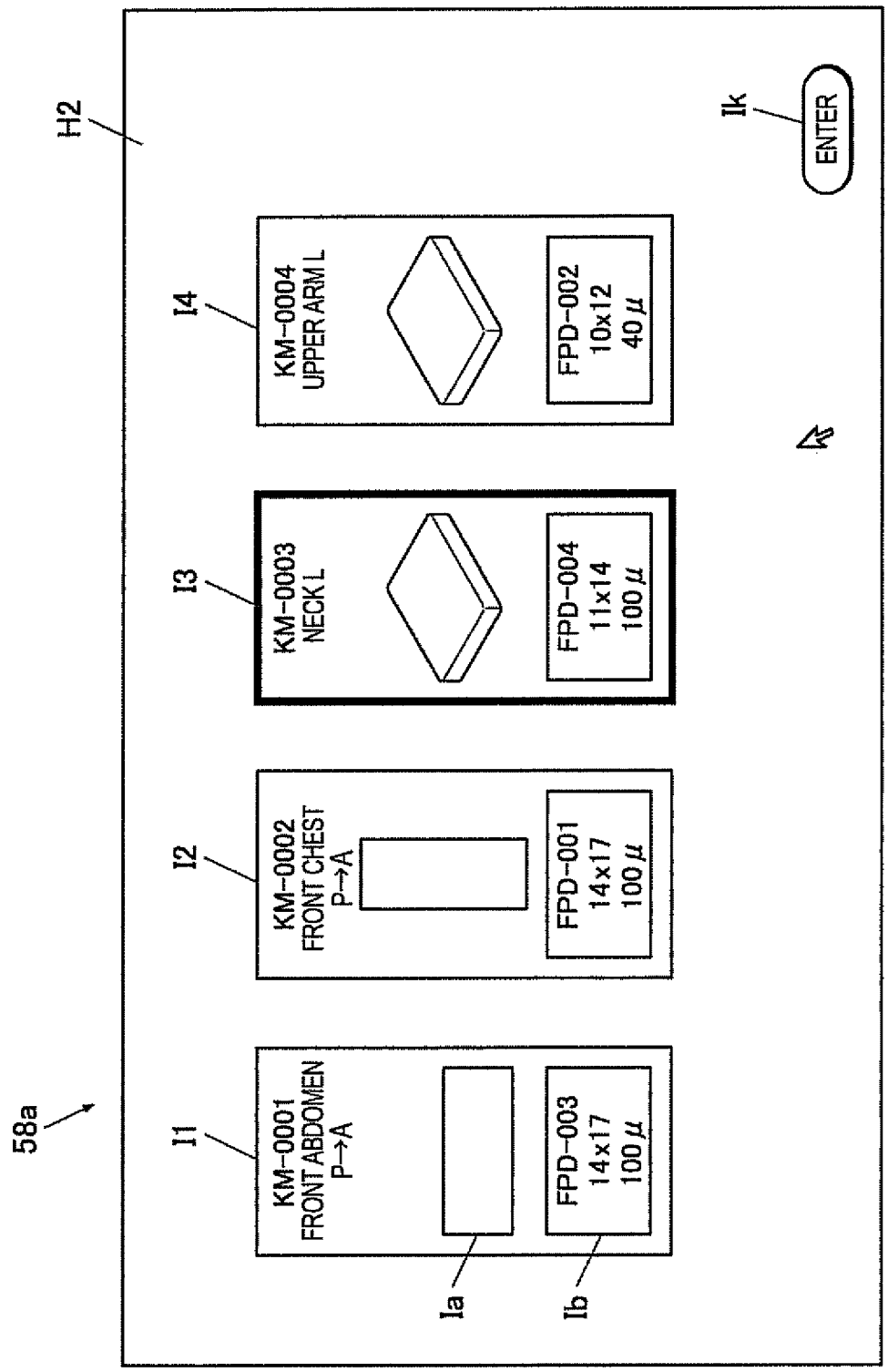
FIG. 9 is a diagram showing an example of a screen displaying icons and the like associated with radiographing order information items.

Furthermore, when the operator such as a radiological technologist clicks the selection buttons h12 to select all of four radiographing order information items and then clicks the enter button h13, for example, the console 58 displays a screen H2 as shown in FIG. 9 on the display unit 58a to display icons I1 to I4 associated with the selected four radiographing order information items on the screen H2 as described above.

In the present embodiment, the "radiographing order ID" P1 (see FIGS. 7 and 8) of the associated radiographing order information item is displayed in a form of "KM-0001", etc. and the "radiographed site" P7 and the "radiographing direction" P8 of the associated radiographing order information item are displayed in a form of "front abdomen P→A", etc. on each of the icons I. Furthermore, in a display part Ia of each icon I, a vertically long rectangle is displayed when the bucky apparatus 51A for radiographing in a standing position (the bucky ID being "001") is to be used, an horizontally long rectangle is displayed when the bucky apparatus 51B for radiographing in a recumbent position (the bucky ID being "002") is to be used, or a figure in perspective view of the radiographic imaging apparatus 1 is displayed when the radiographic imaging apparatus 1 is to be used in the stand-alone state (the bucky ID being "000") depending on the "bucky ID" P9 specified by the radiographing order information item associated with the icon I (that is, the bucky apparatus 51 to be used for radiographing).

Furthermore, in a display part Ib of each icon I, the "FPD size" P10 specified by the associated radiographing order information item, the cassette ID ("FPD-003", etc.) of the radiographic imaging apparatus 1 mounted on the bucky apparatus 51 or in the stand-alone state and the resolution of the radiographic imaging apparatus 1, etc. are displayed. Alternatively, the cassette ID, the resolution, etc. may be displayed by colors and patterns as described above instead of or in combination with the display by characters as described above, or may be announced by using sound such as voice. With such a configuration, the operator such as a radiological technologist can know the size, etc. of the radiographic imaging apparatus to be used at a glance.

In the meantime, to clearly indicate which icon I the next radiographing is associated with to the operator such as a radiological technologist, the console 58 displays the icon I (the icon I3 in the case of FIG. 9) associated with a radiographing order information item on the next radiographing to be conducted in a focused manner by displaying the icon I by using a color different from those of the other icons I or by displaying the icon I with a border of a predetermined color so that the icon I is highlighted as shown in FIG. 9 in the present embodiment. Thus, in the present embodiment, the radiographing order information item associated with the icon I displayed in a focused manner is the radiographing order information specified as the information on the radiographing to be conducted next by the console 58.

When the console 58 displays the icon I in a focused manner, the console 58 may switch the focused display of the icon I sequentially (that is, in the order of registration of the radiographing order information items) in ascending order of the "radiographing order IDs" P1 (see FIGS. 7 and 8) each time radiographing is completed to indicate which radiographing is to be conducted next to the operator such as the radiological technologist by the focused display of the icon I.

Furthermore, as in the radiographic imaging system disclosed in WO 2011/142157 A1 described above, for example, the console 58 may select a radiographing order information item specifying radiographing conditions under which radiographing can be conducted with the smallest degree of change from the current conditions of the special-purpose or portable radiographic imaging apparatus 1 and the radiation source 52 for the radiation generating apparatus 57 present in the radiography room Ra (that is, conditions such as which radiographic imaging apparatus 1 is powered on and in which direction the radiation source 52 is oriented) on the basis of the current conditions, and switch the focused display to the icon I associated with the selected radiographing order information item. As mentioned above, refer to WO 2011/142157 A1 for details of the above.

Furthermore, in the present embodiment, when the operator such as a radiological technologist intends to conduct radiographing different from radiographing associated with the icon I automatically displayed in a focused manner by the console 58, priority is given to the intention of the operator and the focused display is switched to the icon I associated with the radiographing intended to be conducted by the operator, similarly to the radiographic imaging system disclosed in WO 2011/142157 A1 described above. With such a configuration, such a problem as described above may be caused, which will be described later.

When preview image data Dp is to be transmitted to the console 58 before transmitting the image data D, etc. from the radiographic imaging apparatus 1 as described above, for example, after radiographing is conducted in a state where a certain icon I is displayed in a focused manner, the console 58 generates a preview image on the basis of the transmitted preview image data Dp and displays the generated preview image on or near the icon I displayed in the focused manner or in a predetermined display part, which is not shown.

Furthermore, as described above, when the image data D, the offset data O, etc. are transmitted from the radiographic imaging apparatus 1 after radiographing, the console 58 performs image processing such as gain correction, defective pixel correction, and gradation processing depending on the radiographed site to generate a radiographic image. Alternatively, the process of generating a radiographic image may be performed in an image processing apparatus separate from the console 58.

After generating the radiographic image, the console 58 then displays the generated radiographic image on or near the icon I displayed in the focused manner or in a predetermined display part, which is not shown. When the operator such as a radiological technologist looking at the radiographic image approves the radiographic image and conducts a determination operation by clicking an enter button icon Ik (see FIG. 9), the console 58 associates the radiographic image with the associated radiographing order information to perform a determination process. Although not shown in FIG. 9, the operator may be allowed to modify the image quality (contrast, etc.) of the radiographic image generated by the console 58 by operation on the display unit 58*a* of the console 58 before the determination operation.

Note that the focused display of the icon I may be switched to an icon I associated with a radiographing order information item on the next radiographing at the point when the operator such as a radiological technologist confirms a displayed preview image (including a case where the intention of disapproval is not indicated such as a case where a re-radiographing button is not clicked in addition to positive confirmation such as a case where a confirmation button is clicked) of at a point when the operation for determining the radiographic image generated by the console 58 is completed. Furthermore, the present invention can also be applied to a method of switching the focused display individually in the display part of a preview image and in the display part relating to determination of a radiographic image (refer to JP 2010-148720 A, for example) instead of the method of switching the focused display to the next radiographing order information item at the point when such confirmation of the preview image or such determination operation is completed.

[Regarding Configuration, etc. Unique to Present Invention]

Next, a configuration, etc. of the radiographic imaging system 50 according to the present embodiment unique to the present invention will be described. An operation of the radiographic imaging system 50 according to the present invention will also be described.

As described above, in the radiographic imaging system 50 according to the present embodiment, similarly to the radiographic imaging system disclosed in WO 2011/142157 A1 described above, when the operator such as a radiological technologist intends to conduct radiographing different from radiographing associated with the icon I automatically displayed in a focused manner by the console 58, priority is given to the intention of the operator and the focused display is switched to the icon I associated with the radiographing intended to be conducted by the operator. With such a configuration, however, the problem as described above may be caused.

Specifically, when the operator such as a radiological technologist presses the power switch 37 or the selection switch 38 of the radiographic imaging apparatus of 10×12 inches in the radiography room to conduct radiographing associated with the icon 13 in the state shown in FIG. 9, for example, the console 58 determines that the operator intends to conduct radiographing associated with the icon I4 using the radiographic imaging apparatus of 10×12 inches associated with the icon I4 and switches the focused display to the icon I4. The operator, however, radiographs the "neck" of the patient by using the radiographic imaging apparatus of 10×12 inches, and a problem that the console 58 associates the radiographic image of the "neck" generated on the basis of transmitted image data D, etc. with the radiographing order information time specifying radiographing of the "upper arm" associated with the icon I4 occurs.

In this manner, with the radiographic imaging system 50 according to the present embodiment with the configuration described above, the problem that switching of the focused display of the icon I that is not intended by the operator such as a radiological technologist occurs at the console 58 and a generated radiographic image and radiographing order information item are associated with each other by mistake may also occur as described above. In the radiographic imaging system 50 according to the present embodiment, the following configuration is therefore employed, for example, to prevent occurrence of the problem described above. In the following, some examples of such a configuration will be described.

Configuration Example 1

In a configuration example 1, the operator such as a radiological technologist that is a user can conduct at least first operation and second operation on the radiographic imaging apparatus 1, and the radiographic imaging apparatus 1 is configured to transmit a first signal to the console 58 when the first operation is conducted and transmit a second signal different from the first signal to the console 58 when the second operation is conducted.

The operation of the operator on the radiographic imaging apparatus 1 may be operation on the selection switch 38 of the radiographic imaging apparatus 1, for example, and the operator may press the selection switch 38 for a short time (that is, what is called short press) as the first operation and press the selection switch 38 for a longer time (that is, what is called long press) as the second operation.

Although such a configuration will be described in the following, the first operation and the second operation are not limited to short press and long press as long as the operations are recognized as different operations by the radiographic imaging apparatus 1. For example, the operator may press the selection switch 38 once as the first operation and press the selection switch 38 multiple times (twice, for example) as the second operation. Furthermore, although the first and second operations are distinguished from each other by using different operations on one selection switch 38 as described above since the radiographic imaging apparatus 1 is provided with only one selection switch 38 as shown in FIG. 2 in the present embodiment, two selection switches may be provided and the first and second operations may be distinguished from each other by pressing different selection switches. Furthermore, the first and second operations of the operator on the radiographic imaging apparatus 1 are not limited to operations on the selection switches 38 as long as the first and second operations can be distinguished from each other.

Figure 11:
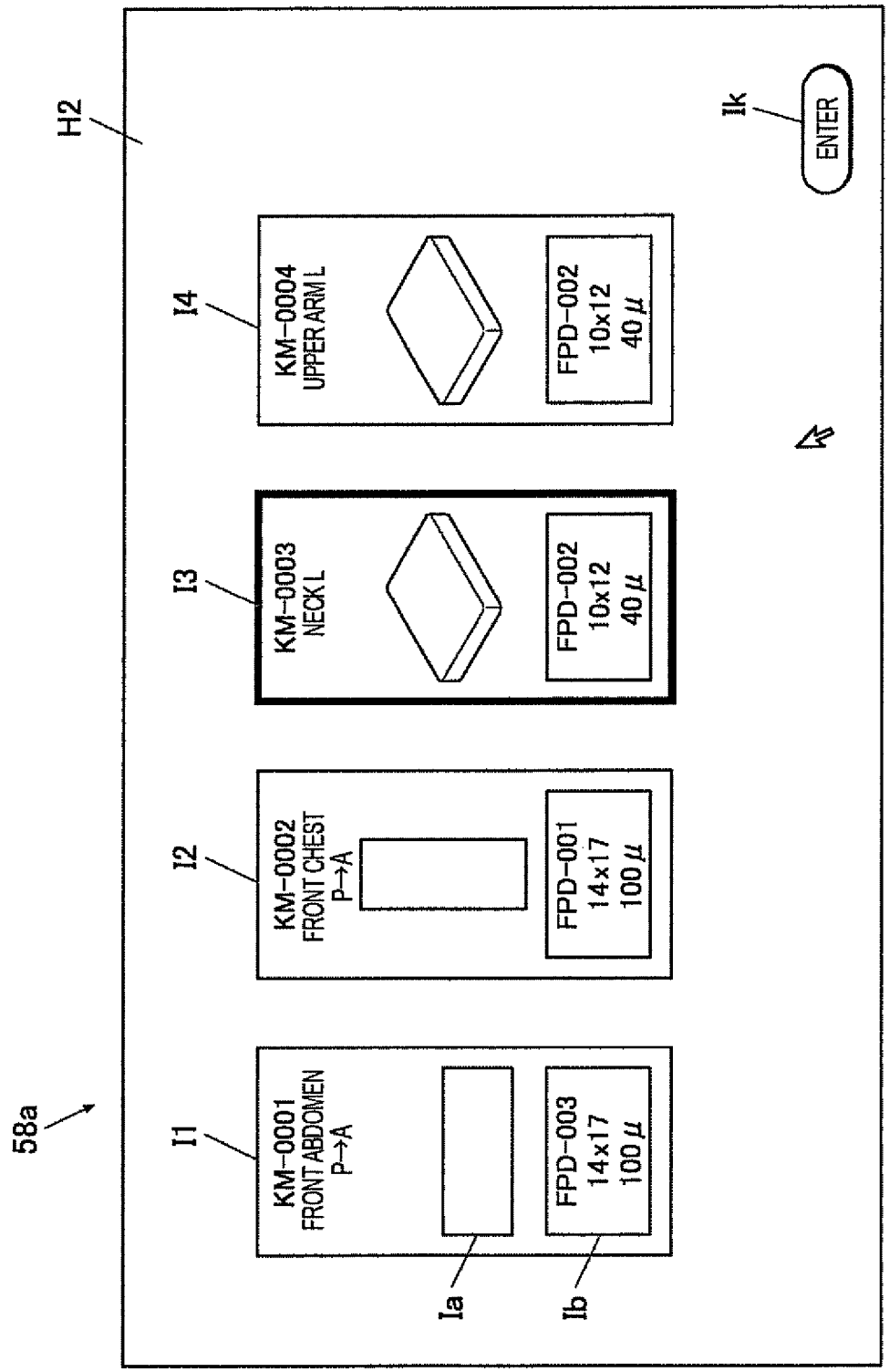
FIG. 11 is a diagram showing a state in which focused display of icons is not changed but display in an icon I3 is changed from the state of FIG. 9.

In addition, in the configuration example 1, the operator such as a radiological technologist conducts the first operation by pressing the selection switch 38 of the radiographic imaging apparatus 1 of 10×12 inches in a state as shown in FIG. 9, for example, and upon receiving the first signal transmitted from the radiographic imaging apparatus 1, the console 58 changes specification of the "FPD size" P10 that is information on the radiographic imaging apparatus in the radiographing order information associated with the icon I3 specified as the radiographing to be conducted next in a focused manner to the size "10×12" that is information on the radiographic imaging apparatus 1 as shown in FIG. 10. The console 58 also changes the display on the size in the icon I3 displayed in the focused manner to "10×12" as shown in FIG. 11. In this case, the focused display of the icon I3 is not switched to the icon I4.

Specifically, the first operation on the radiographic imaging apparatus 1 and the first signal transmitted on the basis of the first operation are operation and signal used by the operator such as a radiological technologist to request the console 58 to change the specification of the information (size) of the radiographic imaging apparatus in the radiographing order information associated with the icon I displayed in the focused manner to the information (size) of the radiographic imaging apparatus 1 whose selection switch 38 is operated by the operator without switching the focused display of the icon I.

In other words, the operator such as a radiological technologist conducts the first operation on the radiographic imaging apparatus 1 when the operator intends to changes the specification of the information (size) of the radiographic imaging apparatus in the radiographing order information without switching the focused display of the icon I, that is, without changing the radiographing to be conducted next to different radiographing. The console 58 then changes the specification of the information (size) of the radiographic imaging apparatus in the radiographing order information associated with the icon I specified by being displayed in a focused manner as radiographing to be conducted next to the information (size) of the radiographic imaging apparatus 1 according to the first operation.

[Effects]

With the radiographic imaging system 50 according to the present embodiment with the configuration as described above, the operator such as a radiological technologist can conduct the first operation on the radiographic imaging apparatus 1 to properly change specification of information on the radiographic imaging apparatus 1 in the radiographing order information associated with an icon I to the information on the radiographic imaging apparatus 1 on which the first operation is conducted without switching the focused display of the icon I. It is therefore possible to properly prevent switching of focused display of an icon I that is not intended by the operator at the console 58.

When the operator such as a radiological technologist conducts radiographing of the "neck" of the patient, for example, by using the radiographic imaging apparatus 1 specified after the change, image data D, etc. of the "neck" are transmitted from the radiographic imaging apparatus 1 to the console 58, and a radiographic image of the "neck" is generated by the console 58. The radiographic image of the "neck" is then properly associated with the radiographing order information specifying radiographing of the "neck" associated with the icon I3. With the configuration described above, a generated radiographic image and radiographing order information can therefore be correctly associated with each other.

Configuration Example 2

In a modification of the configuration example 1, for example, the specification of the information (size) on the radiographic imaging apparatus in the radiographing order information associated with the icon I (the icon I3 in the example of FIG. 11) displayed in a focused manner to the information on the radiographic imaging apparatus 1 on which the first operation is conducted as described above, and at the same time, when other radiographing order information items specifying the information on the radiographic imaging apparatus before the change as described above are present in the radiographing order information items specifying radiographing that has not been not conducted, the specifications of the information on the radiographic imaging apparatus in the radiographing order information items may also be changed to the information on the radiographic imaging apparatus 1.

Figure 12:
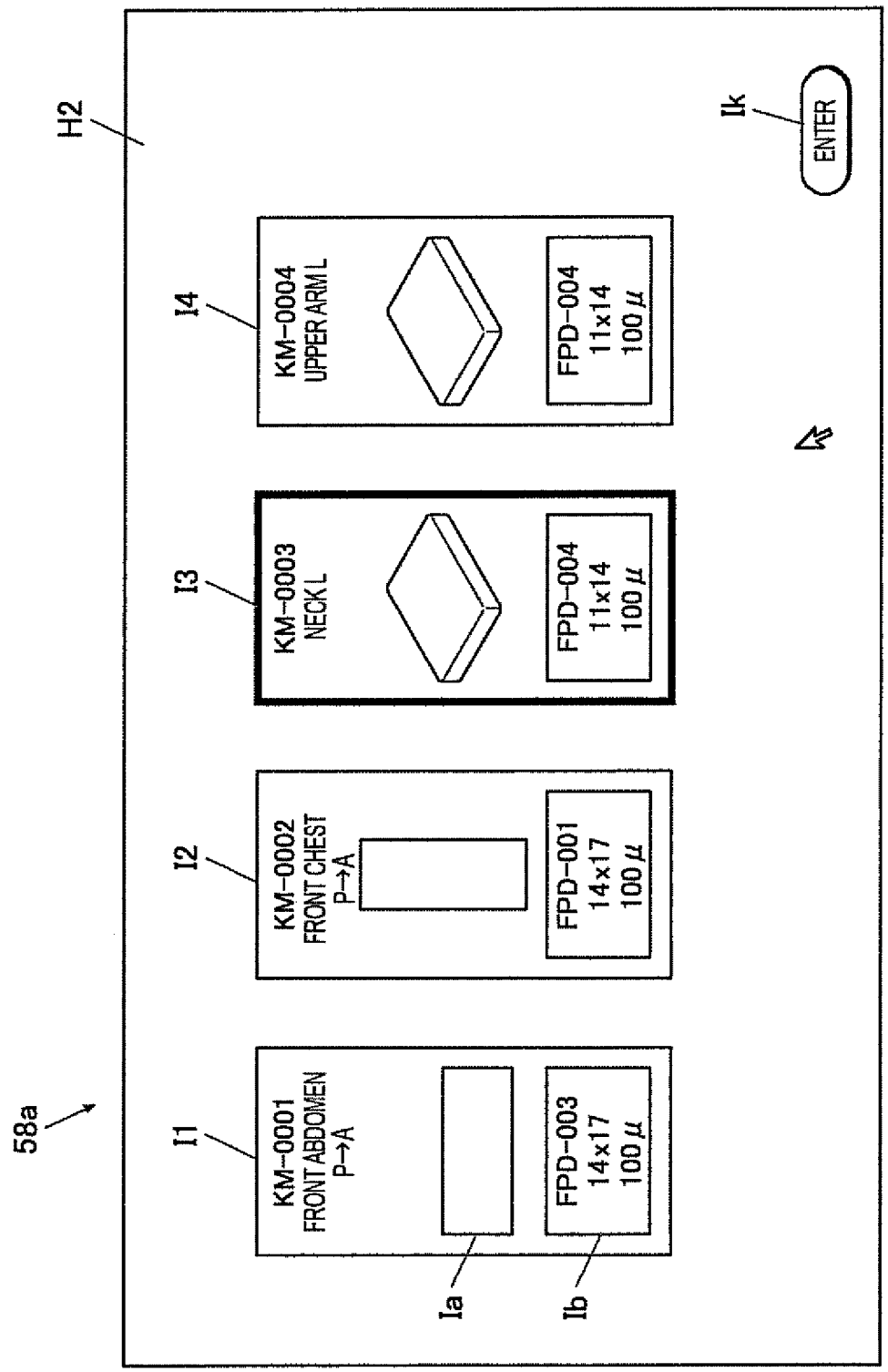
FIG. 12 is a diagram showing an example of display of icons and the like when radiographic imaging apparatuses having the same size are specified by radiographing order information items associated with icons I3 and I4.

Specifically, when "11×14" is specified as the information (size) on the radiographic imaging apparatus in both of the radiographing order information items associated with the icons I3 and I4 as shown in FIG. 12, for example, and when the operator such as a radiological technologist conducts the first operation on the radiographic imaging apparatus 1 of 10×12 inches, for example, the information (size) of the radiographic imaging apparatus in the radiographing order information item associated with the icon I3 is changed to the information (size) of the radiographic imaging apparatus 1 as described above.

When the operator such as a radiological technologist conducts radiographing associated with the icon I3 by using the radiographic imaging apparatus 1 of 10×12 inches instead of the radiographic imaging apparatus 1 of 11×14 inches, other radiographing for which use of the radiographic imaging apparatus 1 of 11×14 inches is specified may also be conducted by using the radiographic imaging apparatus 1 of 10×12 inches instead of the radiographic imaging apparatus 1 of 11×14 inches.

Thus, when the operator such as a radiological technologist has conducted the first operation on the radiographic imaging apparatus 1 to change the size of the radiographic imaging apparatus 1 to be used and if other radiographing order information items specifying the size before the change are present in the radiographing order information items specifying radiographing that has not been conducted as described above, the size in the radiographing order information items can also be changed at the same time. In this case, when the operator conducts the first operation on the radiographic imaging apparatus 1 to change the size of the radiographic imaging apparatus 1 to 10×12 inches, for example, in a state shown in FIG. 12, for example, the size of the radiographic imaging apparatus 1 to be used for radiographing associated with the icon I4 is also changed to 10×12 inches in addition to that associated with the icon I3 as shown in FIG. 11, for example.

With such a configuration, the sizes of the radiographic imaging apparatuses 1 to be used (to be precise, the information on the radiographic imaging apparatuses) can be automatically changed according to the intention of the operator that is a user. The radiographic imaging system 50 is therefore easy to use for the operator.

Although a case where the size of the radiographic imaging apparatus 1 is changed only for radiographing associated with the icon I4 in addition to that associated with the icon I3 in FIGS. 11 and 12, the information is changed to use the radiographic imaging apparatus 1 of 10×12 inches for all radiographing for which the radiographic imaging apparatus 1 of 11×14 inches is specified to be used at the same time according to the configuration as described above.

Configuration Example 3

Even if the operator such as a radiological technologist has conducted the first operation on the radiographic imaging apparatus 1 to change the size of the radiographic imaging apparatus 1 to be used for radiographing, however, this may not necessarily mean that the operator intends to change all the specifications of the same size in other radiographing order information items for radiographing that has not been conducted to the changed size.

The console 58 thus changes the specification of the information (size) of the radiographic imaging apparatus in the radiographing order information associated with the icon I (the icon 13 in the example of FIG. 11) displayed in a focused manner as to the information of the radiographic imaging apparatus 1 on which the first operation is conducted according to the first operation on the radiographic imaging apparatus 1 conducted by the operator. At the same time, when other radiographing order information items specifying the information (size) of the radiographic imaging apparatus before the change are present in the radiographing order information times for which radiographing is not completed, the console 58 can inform the operator of the presence of such radiographing order information items by outputting sound or displaying the information on the display unit 58a.

In this case, the console 58 serves as an informing unit, but a speaker or a screen may be provided as the informing unit in the radiography room Ra, for example, to inform the operator in the radiography room Ra instead of the console 58. Furthermore, the radiographic imaging apparatus 1 may serve as the informing unit to announce the above by lighting or making the indicator 40 (see FIG. 2) of the radiographic imaging apparatus 1 blink in a predetermined manner, providing a display unit or providing a speaker on the radiographic imaging apparatus 1.

When predetermined operation is conducted by the operator such as a radiological technologist that is a user, such as the first operation conducted again on the radiographic imaging apparatus 1 by the operator after the announcement (that is, when approval of the operator is provided) or when predetermined cancellation operation has not been conducted by the operator within a predetermined period of time after the announcement, the console 58 then also changes the specifications of the information (size) of the radiographic imaging apparatus for other radiographing order information items to the information (size) of the radiographic imaging apparatus 1.

When the predetermined cancellation operation is conducted by the operator, the console 58 changes the specification of the information (size) of the radiographic imaging apparatus only for the radiographing order information item associated with the icon I (the icon I3 in the example of FIG. 11) displayed in a focused manner to the information on the radiographic imaging apparatus 1 on which the first operation is conducted without changing the specification of the information (size) of the radiographic imaging apparatus for the other radiographing order information items.

With such a configuration, the information (size) of the radiographic imaging apparatus 1 to be used can be automatically changed at the same time or can be left without being changed when such a change is unnecessary according to the intention of the operator that is a user in a more proper manner. The radiographic imaging system 50 is therefore easy to use for the operator.

Configuration Example 4

Note that the announcement described above may be conducted by display on or sound output by a portable terminal, which is not shown, carried by the operator such as a radiological technologist that is a user as the informing unit in the configuration example 3.

In this case, when the operator who has recognized the presence of another radiographing order information item specifying the radiographic imaging apparatus 1 of the same size as a result of the announcement has conducted predetermined operation (that is, when approval of the operator is provided), the portable terminal transmits a signal indicating that the predetermined operation is conducted to the console 58. In this case, when the operator who has determined not to change the size for other radiographing order information items specifying the radiographic imaging apparatus 1 of the same size, the portable terminal transmits a signal indicating that the predetermined cancellation operation is conducted to the console 58.

Upon receiving the signal indicating that the predetermined operation is conducted from the portable terminal, the console 58 then determines that the predetermined operation is conducted by the operator and changes the specification of the information (size) of the radiographic imaging apparatus for the radiographing order information item to the information (size) of the radiographic imaging apparatus 1 on which the first operation is conducted by the operator such as a radiological technologist. When a signal indicating that the predetermined cancellation operation is conducted within a predetermined period of time is received from the portable terminal, the console 58 determines that the predetermined cancellation operation is conducted within the predetermined period of time by the operator and changes the specification of the information (size) of the radiographic imaging apparatus only for the radiographing order information item associated with the icon I displayed in a focused manner to the information on the radiographic imaging apparatus 1 on which the first operation is conducted without changing the specification of the information (size) of the radiographic imaging apparatus for the other radiographing order information item.

With such a configuration, similarly to the configuration example 3 described above, the information (size) of the radiographic imaging apparatus 1 to be used can be automatically changed at the same time or can be left without being changed when such a change is unnecessary according to the intention of the operator that is a user in a more proper manner, and the radiographic imaging system 50 is easy to use for the operator.

Configuration Example 5

When the second operation different from the first operation is conducted on the radiographic imaging apparatus 1 by the operator such as a radiological technologist, the console 58 can switch the focused display of the icon I unlike the configuration examples 1 to 4 described above, for example.

Specifically, when the second operation in a different manner from the first operation is conducted by the operator such as a radiological technologist that is a user, the radiographic imaging apparatus 1 transmits the second signal different from the first signal to the console 58, the console 58 in receipt of the second signal from the radiographic imaging apparatus 1 changes the radiographing order information specified for radiographing to be conducted next to the radiographing order information item specifying the information (size) of the radiographic imaging apparatus 1 among the radiographing order information items for radiographing that has not been conducted.

Figure 13:
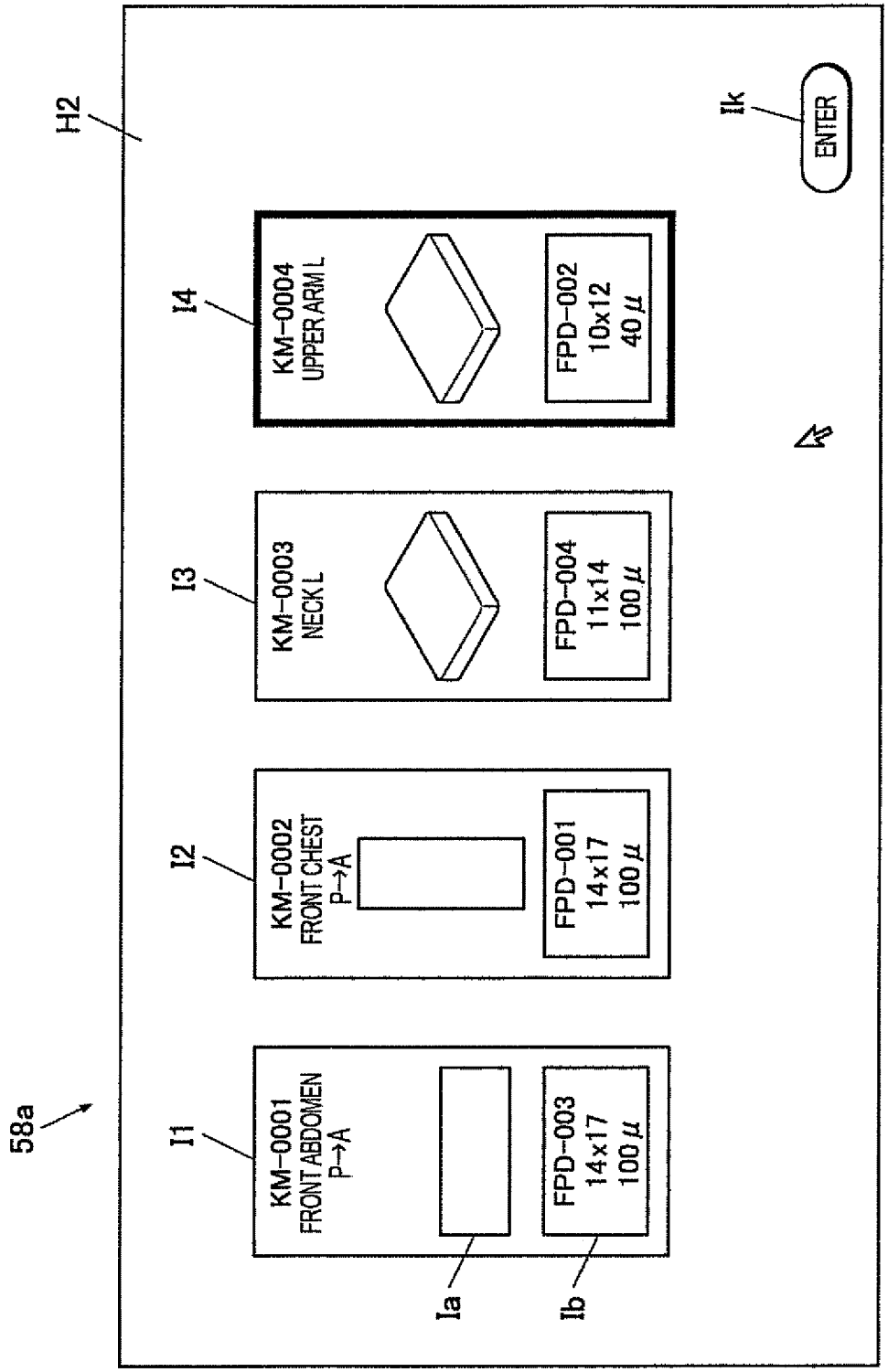
FIG. 13 is a diagram explaining transition of focused display of icons from the state of FIG. 9 in a configuration example 5.

Thus, when the operator such as a radiological technologist conducts the second operation (such as pressing the selection switch 38 for a long time) on the radiographic imaging apparatus 1 of 10×12 inches in the state shown in FIG. 9, for example, the console 58 switches the focused display of the icon I3 determined for radiographing to be conducted next to the icon I4 associated with the radiographing order information item specifying that the radiographic imaging apparatus 1 of 10×12 inches is to be used as shown in FIG. 13, for example.

With such a configuration, when the operator such as a radiological technologist intends to change the radiographing order information determined for radiographing to be conducted next (that is, when the operator intends to switch the focused display of the icon I), the operator can easily and properly change the radiographing order information (that is, switch the focused display of the icon I) by conducting the second operation on the radiographic imaging apparatus 1 having the size specified by the radiographing order information item to be changed to (that is, the radiographing order information item associated with the icon I to which the focused display is switched to). Since the operator can switch the focused display only by conducting the second operation (pressing the selection switch 38 for a long time, for example) on the radiographic imaging apparatus 1 in the radiography room Ra without moving into the anteroom Rb (see FIG. 1) and operating the console 58 to switch the focused display, the radiographic imaging system 50 is easy to use for the operator.

Configuration Example 6

In the configuration example 5 described above, unintended switching of focused display may also occur in such a case where the first operation such as pressing of the selection switch 38 for a short time that is intended to be conducted on the radiographic imaging apparatus 1 by the operator such as a radiological technologist is determined to be the second operation such as pressing of the selection switch 38 for a long time by the radiographic imaging apparatus 1.

Thus, in the configuration example 5, similarly to the configuration example 3, the console 58 may be configured to inform the operator such as a radiological technologist that the focused display is to be switched (to be precise, that the radiographing order information item determined for radiographing to be conducted next is to be changed to the radiographing order information item specifying the information on the radiographic imaging apparatus 1 among the radiographing order information items for which radiographing has not been conducted) by outputting sound or displaying the information on the display unit 58a, announcing the information from an informing unit provided in the radiography room Ra or the like, or using the radiographic imaging apparatus 1 itself as the informing unit, for example, instead of switching the focused display upon receiving the second signal from the radiographic imaging apparatus 1.

Then, the focused display of the icon I (the icon I3, for example) may be switched to another icon I (icon I4, for example) only when predetermined operation is conducted by the operator such as a radiological technologist that is a user, such as the second operation conducted again on the radiographic imaging apparatus 1 by the operator after the announcement (that is, when approval of the operator is provided) or only when predetermined cancellation operation has not been conducted by the operator within a predetermined period of time after the announcement.

With such a configuration, focused display can be switched or can be left without being switched when the switching is not to be conducted according to the intention of the operator that is a user in a more proper manner. The radiographic imaging system 50 is therefore easy to use for the operator.

Configuration Example 7

Furthermore, in the configuration example 6 described above, similarly to the configuration example 4, the announcement described above may be conducted by display on or sound output by a portable terminal, which is not shown, carried by the operator such as a radiological technologist that is a user as the informing unit. The portable terminal is configured to transmit a signal indicating that predetermined operation is conducted to the console 58 when the predetermined operation is conducted by the operator, and to transmit a signal indicating that predetermined cancellation operation is conducted to the console 58 when the predetermined cancellation operation is conducted by the operator. When the signal indicating that the predetermined operation is conducted is received from the portable terminal, the console 58 determines that the predetermined operation is conducted by the operator, or when the signal indicating that the predetermined cancellation operation is conducted by the operator within a predetermined period of time is received from the portable terminal, the console 58 determines that the predetermined cancellation operation is conducted by the operator within the predetermined period of time.

Then, with such a configuration, only when predetermined operation is conducted on the portable terminal by the operator such as a radiological technologist (that is, when approval of the operator is provided) after the announcement, or only when predetermined cancellation operation has not been conducted on the portable terminal by the operator within a predetermined period of time after the announcement, the focused display of the icon I (the icon I3, for example) is switched to another icon I (icon I4, for example). Thus, similarly to the configuration example 6, focused display can be switched or can be left without being switched when the switching is not to be conducted according to the intention of the operator that is a user in a more proper manner, and the radiographic imaging system 50 is easy to use for the operator.

Summary of Configuration Examples 1 to 7

The configuration examples 1 to 7 described above may be employed alone or may be employed in combination. It is then determined in advance as follows: when only the specification of the information (size) of the radiographic imaging apparatus in the radiographing order information is to be changed without switching the focused display of the icon I, the operator such as a radiological technologist conducts the first operation (presses the selection switch 38 for a short time, for example) on the radiographic imaging apparatus 1 (in the cases of the configuration examples 1 to 4), and when the focused display of the icon I is to be switched to the icon I specifying the size of the radiographic imaging apparatus 1 operated by the operator, the operator conducts the second operation (presses the selection switch 38 for a long time, for example) on the radiographic imaging apparatus 1 (in the cases of the configuration examples 5 to 7) as described above.

With such a configuration, the operator such as a radiological technologist can change only the specification of the information (size) of the radiographic imaging apparatus 1 in the radiographing order information without switching the focused display of the icon I or switch the focused display of the icon I only by conducting the first operation or the second operation on the radiographic imaging apparatus 1.

Thus, switching of the focused display of the icon I that is not intended by the operator such as a radiological technologist at the console 58 can be properly prevented, and the focused display if the icon I can be properly switched when the focused display is intended. As a result, the console 58 can correctly associate a generated radiographic image with radiographing order information, and the radiographic imaging system 50 is very easy to use for the operator.

Modified Example 1

Note that the portable terminal described in the configuration examples 4 and 7 may have functions equivalent to those of the console 58 or may have some predetermined functions of those of the console 58 so that various processes can be executed at the portable terminal.

Modified Example 2

Furthermore, although the operator such as a radiological technologist conducts the first or second operation on the radiographic imaging apparatus 1 to switch or not to switch the focused display of the icon I in the [Summary of Configuration Examples 1 to 7] described above, the console 58 may be configured not to switch the focused display of the icon I and conduct only the process of changing the specification of the information (size) on the radiographic imaging apparatus in the radiographing order information associated with the icon I displayed in a focused manner when the operator has conducted operation such as operating the selection switch 38 of the radiographic imaging apparatus 1, for example. In this case, the length of the period during which the selection switch 38 of the radiographic imaging apparatus 1 is pressed is not distinguished and the console 58 is configured to execute the process described above when operation is conducted on the radiographic imaging apparatus 1, for example.

With such a configuration, at least switching of the focused display of the icon I that is not intended by the operator such as a radiological technologist at the console 58 can be reliably prevented. As a result, the console 58 can correctly associate a generated radiographic image with radiographing order information.

In addition, when the first and second operations are not distinguished from each other and when the portable terminal is used in combination as described above, a pressure sensor (refer to JP 2009-172242 A), an accelerometer (refer to JP 2005-003755 A), a proximity sensor (refer to JP 2002-191586 A), etc. may also be used as a unit for detecting the intention of the operator such as a radiological technologist to conduct radiographing by using another radiographic imaging apparatus in addition to the selection switch 38 of the radiographic imaging apparatus 1 described above. The above unit may be the power switch 37 of the radiographic imaging apparatus 1, and turning on of the power switch 37 of the radiographic imaging apparatus 1 that has been off may be regarded as the intention of the operator to use the radiographic imaging apparatus 1.

Although cases where information on the radiographic imaging apparatus in radiographing order information is the size of the radiographic imaging apparatus 1 and the size of the radiographic imaging apparatus 1 changed as the change in the specification of the information on the radiographic imaging apparatus 1 are described in the embodiment described above, the present invention can alternatively be applied to cases where the resolution (that is, the pixel size) is changed for capturing a high-resolution image, the scintillator type is changed for reducing the amount of irradiation, or a combination of the size, the resolution (pixel size), and the scintillator type is changed, for example, as the change in the specification of the information on the radiographic imaging apparatus.

In such cases, similarly to the embodiment described above, the specification (size, resolution, scintillator type, etc.) of each radiographic imaging apparatus 1 is preferably displayed in the display part Ib of each icon I using different colors, patterns, etc. of the icons so that the operator such as a radiological technologist can know the specification of each radiographic imaging apparatus at a glance.

It should be appreciated that the present invention is not limited to the embodiment, configuration examples, modified examples, etc. described above, but can be modified as appropriate without departing from the scope of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiographic imaging system comprising:
a plurality of multiple radiographic imaging apparatuses each including a plurality of radiation detecting elements arranged two-dimensionally, and configured to read charges generated in the radiation detecting elements as a result of irradiation with radiation as image data; and
a console configured to register a plurality of radiographing order information items each including information indicating which of the plurality of radiographic imaging apparatuses is to be used for conducting radiographing, or acquire the plurality of registered radiographing order information items,
wherein each of the plurality of radiographic imaging apparatuses includes an input switch that is operated by a user and outputs a first signal when the input switch is operated, and
wherein upon receiving the first signal from one of the plurality of radiographic imaging apparatuses, the console changes specification of information on the radiographic imaging apparatus in the radiographing order information item determined for radiographing to be conducted next to information on the radiographic imaging apparatus from which the signal is received without switching the radiographing order information item to another radiographing order information item, and changes specification of information on the radiographic imaging apparatus in another radiographing order information item specifying information on the radiographic imaging apparatus before the change among the radiographing order information items for which radiographing has not been conducted to the information on the radiographic imaging apparatus from which the signal is received.

2. The radiographic imaging system according to claim 1, wherein the console changes specification of information on the radiographic imaging apparatus in the radiographing order information item determined for radiographing to be conducted next to the information on the radiographic imaging apparatus from which the signal is received, and when another radiographing order information item specifying information on the radiographic imaging apparatus before the change is present among the radiographing order information items for which radiographing has not been conducted, the console makes an informing unit announce the presence of the radiographing order information item, and when predetermined operation is conducted by the user or when predetermined cancellation operation has not been conducted by the user within a predetermined period of time after the announcement, the console changes the specification of the information on the radiographic imaging apparatus in the other radiographing order information item to the information on the radiographic imaging apparatus from which the signal is received.

3. The radiographic imaging system according to claim 2, wherein the informing unit is a portable terminal carried by the user, when the predetermined operation or the predetermined cancellation operation is conducted on the portable terminal by the user, the portable terminal transmits a signal indicating that the predetermined operation has been conducted or a signal indicating that the predetermined cancellation operation has been conducted to the console, and when the signal indicating that the predetermined operation has been conducted is received from the portable terminal, the console determines that the predetermined operation has been conducted by the user, or when the signal indicating that the predetermined cancellation operation has been conducted within a predetermined period of time is received from the portable terminal, the console determines that the predetermined cancellation operation has been conducted by the user within a predetermined period of time.

* * * * *